United States Patent [19]

Heymès

[11] 4,145,552
[45] Mar. 20, 1979

[54] PREPARATION OF VINCAMINE AND RELATED ALKALOIDS

[75] Inventor: Alain Heymès, Portet, Garonne, France

[73] Assignee: Parcor, Paris, France

[21] Appl. No.: 812,473

[22] Filed: Jul. 5, 1977

[30] Foreign Application Priority Data

Jul. 13, 1976 [FR] France .................. 76 21432

[51] Int. Cl.² .......................................... C07D 519/04
[52] U.S. Cl. ...................................................... 546/51
[58] Field of Search ................... 260/293.53, 293.55

[56] References Cited

U.S. PATENT DOCUMENTS

| 3,799,933 | 3/1974 | Le Men et al. | 260/293.53 |
| 3,979,395 | 9/1976 | Taccone | 260/293.53 |

FOREIGN PATENT DOCUMENTS 763730  8/1971  Belgium.

Primary Examiner—Natalie Trousof
Assistant Examiner—Richard A. Schwartz
Attorney, Agent, or Firm—Cushman, Darby & Cushman

[57] ABSTRACT

A process for preparing vincamine and related alkaloids, comprising reacting a compound of formula:

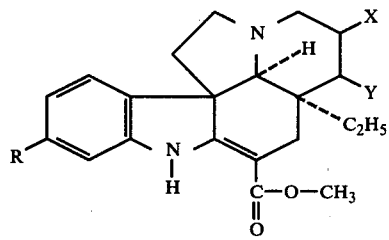

(wherein R is H or methoxy and X and Y are hydrogen or together represent a double bond between the carbon atoms to which they are bonded) with a carbanion-forming agent in a reaction medium; then introducing oxygen into the reaction medium until saturation point, a reducing agent compatible with oxygen being added to the reaction medium before the medium ceases absorbing oxygen; acidifying the mixture and extracting therefrom a mixture of compounds

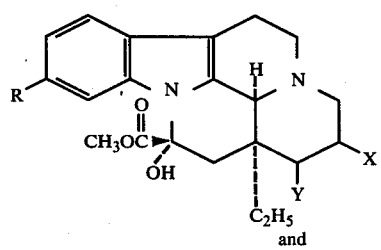

and

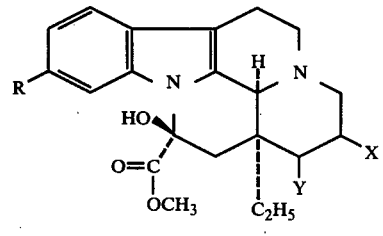

7 Claims, No Drawings

PREPARATION OF VINCAMINE AND RELATED ALKALOIDS

The interest in the preparation of vincamine from tabersonine and vincadiformine and the problems presented by this semisynthesis can be seen from Belgian Pat. No. 832,157.

It has been proposed to eliminate these problems by means of an oxidation process using oxygen in the presence of iron, cobalt or copper salts. The reaction takes at least 5 days.

The invention can shorten this period to a few hours, whilst retaining the advantages of conversion in a single, homogeneous industrial stage.

The process according to the invention for preparing vincamine and related alkaloids comprises reacting a compound of formula:

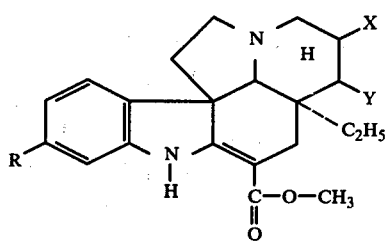

(wherein R is H or methoxy and X and Y are hydrogen or together represent a double bond between the carbon atoms to which they are bonded) with a carbanion-forming agent in a reaction medium, then introducing oxygen into the reaction medium until saturation point, a reducing agent compatible with oxygen being added to the reaction medium before the medium stops absorbing oxygen; acidifying the mixture and extracting therefrom a mixture of compounds of formula:

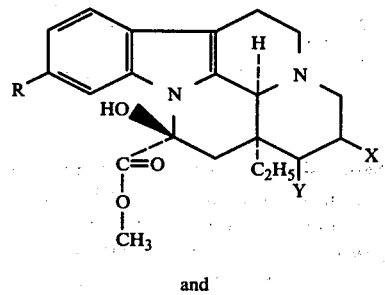

and

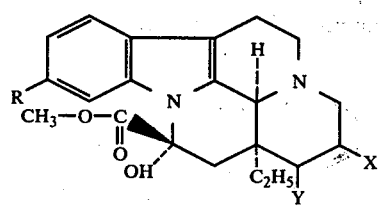

and separating these two compounds from each other; compounds wherein X and Y represent a double bond being optionally reduced at any desired stage after the point when the absorption of oxygen ceases.

A mixture of vincamine and 16-epi-vincamine (R=X=Y=H) is generally obtained in the same reactor in a few hours, the reduction stage only being necessary if the reaction starts from a tabersonine derivative.

The process of the invention will be described in more detail hereinafter, referring to the various stages. It should be understood that these stages can occur in the same reactor without isolating the intermediate products, right up to the separation.

The various stages of the process can be illustrated by the following reaction scheme,

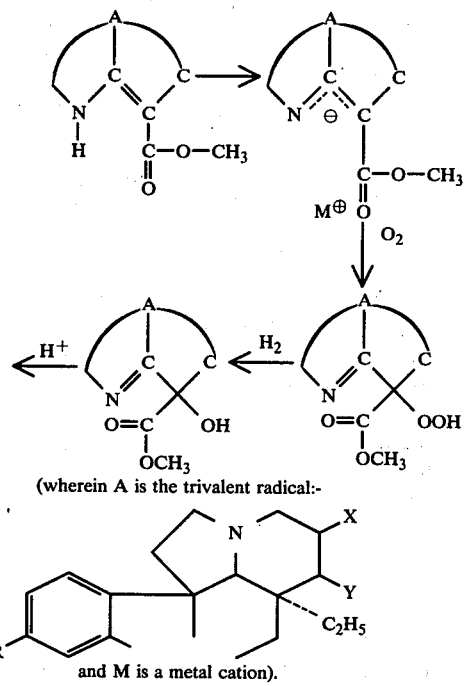

(wherein A is the trivalent radical:- and M is a metal cation).

In the first stage of the process, carbanions are formed.

For this purpose, a base, such as an alkali metal hydride (particularly sodium, lithium or potassium hydride), an alkali metal amide or alkylamide (especially a dialkylamide with up to 12 carbon atoms, such as lithium diisopropylamide), and alkali metal alkylsilylamides (particularly lithium and sodium bis-(trialkylsilyl)-amides), is used. Alkali or alkaline earth metal alcoholates such as lithium methoxide, sodium methoxide, potassium methoxide, magnesium methoxide, potassium t-butoxide and sodium t-amylate can also be used.

The base is generally used in slight excess, for example a 10% excess, over the stoichiometric quantity.

The reaction is preferably carried out at between $-80°$ C. and $+50°$ C., preferably nearer the bottom of this range. It generally takes from 5 minutes to 12 hours. The preferred solvents are dimethylformamide, dimethyl sulphoxide, 4- to 8-membered heterocyclic compounds interrupted by an oxygen atom (such as tetrahydrofuran), hydrocarbons (particularly alkanes), alcohols, amides and aromatic hydrocarbons (such as benzene, toluene and xylenes).

In the second stage of the process the carbanion is oxidised to form a hydroperoxide. This is effected with oxygen, e.g. at a pressure of from 1 to 10 kg/cm² over a period of from 5 minutes to 12 hours. The reaction proceeds satisfactorily at for example between $-30°$ C. and $+50°$ C.

The oxygen may be used in the form of a mixture of oxygen and an inert gas, such as nitrogen or a rare gas.

In the third stage of the process, the hydroperoxide is reduced to the alcohol in the 16-position.

Advantageously, the reducing agent (which may be an alkylphosphite, especially a trialkylphosphite, an alkali metal borohydride, the salts where the metal is in a lower state of oxidation, such as stannous or ferrous chlorides, etc.) is added to the reaction medium before the oxygen is introduced. This reduction is generally carried out at between −30° and +50° C.

In the fourth stage of the process, the medium is acidified. For this purpose, a dilute inorganic acid (such as a ½N solution of hydrochloric acid) or an organic acid (such as acetic acid) is added, for example at between 0° and 100° C. over a period of between 5 minutes and 12 hours.

In the fifth stage of the process, the reaction mixture is extracted. This extraction may be carried out by making the medium alkaline again (for example by the addition of ammonia until an alkaline pH is obtained), then extracting with an organic solvent, such as chlorinated hydrocarbons, particularly chlorinated alkanes such as chloroform or methylene chlorine. The solvent is then removed by evaporation.

The compounds are then separated by chromatography, especially on silica gel.

If necessary, conventional catalytic hydrogenation is carried out to convert the compounds wherein X and Y are not hydrogen into saturated compounds.

The following Examples illustrate the invention.

EXAMPLE 1

Preparation of (+)-vincamine and (+)-16-epivincamine from (−)-vincadiformine

At ambient temperature, over a period of thirty minutes, a solution of 33.8g (0.1 mol) of (−)-vincadiformine in a mixture of 140ml of anhydrous dimethylformamide and 140ml of anhydrous toluene is added to a suspension of 2.64g (0.11 mol) of sodium hydride in a mixture of 200ml of anhydrous tetrahydrofuran, 20ml of anhydrous hexamethylphosphotriamide (EMPT) and 18.7 ml (0.14 mol) of trimethylphosphite. When the release of hydrogen has finished (about two hours later), the solution is cooled to −10° C. and then stirred under an oxygen atmosphere until absorption ceases (duration: 3 hours). Still at −10° C., 136 ml of glacial acetic acid are added, and the mixture is then left at ambient temperature for two hours. After the addition of 500ml of 1N sulphuric acid, the aqueous phase is isolated, re-extracted with 150ml of isopropyl ether, made alkaline with 350ml of 11N ammonia, then extracted 3 times with 300ml aliquots of methylene chloride. After drying over calcium chloride and evaporating the solvent, 30.2g of crude product are obtained which, when chromatographed on a column of silica gel (1.5 kg) yield, in the order of elution:

9.9 g of vincamine (yield: 28%) m.p. (decomp.): 250° C.

$[\alpha]_D^{20}$: 41° (c = 1, pyridine)

3.7 g of 16-epivincamine (yield: 10.5%)

m.p.: 185° C.

$[\alpha]_D^{20}$: −36° (c = 1, chloroform)

The I.R., U.V. and N.M.R. spectra of the two products are identical to those of authentic samples.

The preparation takes less than 10 hours in all.

EXAMPLE 2

Preparation of (+)-41,15-dehydrovincamine and (+)-14,15-dehydro-16-epivincamine

Starting from 13.6g (0.04 mol) of (−)-tabersonine, the method is exactly the same as in Example 1. The crude product (10.3g) obtained after treatment and chromatographed on a 500g column of silica gel yields, in order to elution:

3.4 g of 14,15-dehydrovincamine (yield: 24%)

m.p. (decomp.) = 226° C.

$[\alpha]_D^{27}$: +128° C. (c = 1, chloroform)

1.4 g of 14,15-dehydro-16-epivincamine (yield: 10%)

m.p.: 185° C.

$[\alpha]_D^{20}$: +30° (chloroform).

What we claim is:

1. A process for preparing compounds of the formula:

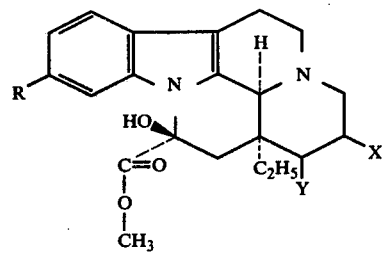

wherein R is hydrogen or methoxy and X and Y are hydrogen or together represent a supplementary valence bond between the carbon atoms to which they are bonded, comprising reacting a compound of formula:

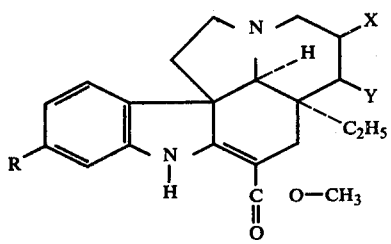

with a carbanion-forming agent in a reaction medium; then introducing oxygen into the reaction medium until the medium ceases absorbing oxygen, a reducing agent compatible with oxygen being added to the reaction medium before the medium ceases absorbing oxygen; then acidifying the mixture and extracting therefrom a mixture of compounds of formula:

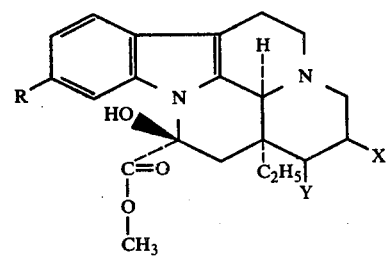

and

-continued

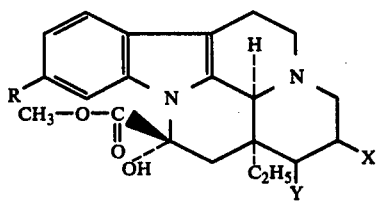

and separating these two compounds from each other; compounds wherein X and Y represent a supplementary bond being optionally reduced at any desired stage after the point when the absorption of oxygen ceases.

2. A process as claimed in claim 1 wherein the carbanion is formed by treatment with an alkali metal hydride, an alkali metal amide, an alkali metal alkylamide, an alkali metal alkylsilylamide, an alkali metal alcoholate or an alkaline earth metal alcoholate at −80° to +50° C. for 5 minutes to 12 hours.

3. A process as claimed in claim 1 wherein the oxidation is effected using oxygen under a pressure of from 1 to 10 kg/cm² at between −30° C. and +50° C. for 5 minutes to 12 hours.

4. A process as claimed in claim 1 wherein the reduction is carried out using a reducing agent of the alkylphosphite or borohydride type or a salt where the metal is in a lower state of oxidation at between −30° and +50° C.

5. A process as claimed in claim 1 wherein the reducing agent is added before the oxygen is introduced.

6. A process as claimed in claim 1 wherein the reaction medium contains as solvent an amide, a sulphoxyde, a heterocyclic compound with 4 to 8 carbon atoms interrupted by an oxygen atom, an alkane, an alkanol or an aromatic hydrocarbon.

7. A process as claimed in claim 1, wherein the medium is acidified by adding a dilute inorganic acid or an organic acid.

* * * * *